United States Patent [19]

Papas et al.

[11] Patent Number: 5,236,828
[45] Date of Patent: Aug. 17, 1993

[54] PLASMID PJL6

[76] Inventors: Takis S. Papas, 10700 Tulip La., Potomac, Md. 20859; James A. Lautenberger, 904 Allan Rd., Rockville, Md. 20850

[21] Appl. No.: 827,877

[22] Filed: Jan. 30, 1992

Related U.S. Application Data

[63] Continuation of Ser. No. 275,573, Nov. 23, 1988, abandoned, which is a continuation of Ser. No. 511,108, Jul. 6, 1983, abandoned.

[51] Int. Cl.[5] .............. C12N 15/73; C12N 15/63; C12N 15/66
[52] U.S. Cl. .................. 435/69.1; 435/320.1; 530/350; 935/27; 935/29; 935/38; 935/40; 935/47
[58] Field of Search ............. 435/69.1, 69.7, 71.1, 435/71.2, 320.1

[56] References Cited

U.S. PATENT DOCUMENTS 4,831,120 5/1989 Aviv et al. .................. 435/69.4 X

OTHER PUBLICATIONS

Renaut et al., 1981, Gene, 15: 81-93.
Oppenheim et al., 1982, J. Mol. Biol. 158: 327-346.
Bolivar et al., 1977, Gene, 2: 95-113.

Primary Examiner—Richard A. Schwartz
Assistant Examiner—Johnny F. Railey, II
Attorney, Agent, or Firm—Cushman, Darby & Cushman

[57] ABSTRACT

The plasmid of this invention contains the cII translation initiation site and a $P_L$ promoter—both are very efficient, producing large amounts of cII protein. This plasmid contains a unique ClaI restriction site in the aminoterminal portion of the cII gene suitable for insertion of foreign genes. This plasmid is an improvement over other plasmids because the inserted genes are subject to the same transcriptional and translational characteristics of the cII gene; this plasmid, therefore, produces large amounts of the protein coded by the exogenous gene.

11 Claims, 3 Drawing Sheets

PLASMID PJL6

This is a continuation of application Ser. No. 07/275,573, filed on Nov. 23, 1988, now abandoned, which in turn is a continuation of application Ser. No. 06/511,108, filed on Jul. 6, 1983, now abandoned.

The plasmid of this invention contains the CII translation initiation site and a $P_L$ promoter—both are very efficient, producing large amounts of cII protein. This plasmid contains a unique ClaI restriction site in the aminoterminal portion of the cII gene suitable for insertion of foreign genes. This plasmid is an improvement over other plasmids because the inserted genes are subject to the same transcriptional and translational characteristics of the cII gene; this plasmid, therefore, produces high large amounts of the protein coded by the exogenous gene.

MATERIAL INFORMATION DISCLOSURE

Cohen et al (U.S. Pat. No. 4,237,224) discloses the method of making plasmid pSC101. Although this plasmid has gained widespread use, proteins produced by the bacteria transformed by pSC101 result in only small quantities of the desired protein. The present invention represents an improvement over the Cohen process. The improvement consists of a plasmid capable of transforming bacteria in such a manner as to produce large amounts of the desired exogene carried on the plasmid.

Derom et al, *Gene*, Vol 17, pp 45–54 (1981) and Jay et al, *PNAS*, Vol. 78, pp 5543–5548 (1981) both disclose the use of plasmid SV40.

Kleid et al, *Science*, Vol. 214, pp 1125–1129 (1981) discloses pFM$_1$, a plasmid designed for use with foot and mouth disease.

Watson et al, *Science*, Vol. 218, pp 381–384 (1982) discloses a plasmid suitable for use with herpes simplex virus type 1.

All of these plasmids—Derom's Jay's, Kleid's and Watson's—are subject to the same problem that affects Cohen's plasmid, i.e, only small quantities of the desired protein are produced.

STATEMENT OF DEPOSIT

The plasmid of this invention has been deposited in the American Type Culture Collection, 12301 Parklawn Drive, Rockville, Md., 20852-1776, on Jan. 31, 1986. The accession number is ATCC 53456.

The plasmid of this invention has been deposited prior to filing this application in the U.S. Government's facilities run by the National Institutes of Health at Frederick, Md. Contact Takis S. Papas or James A. Lautenberger, Laboratory of Molecular Oncology, National Cancer Institute, Bethesda, Md. 20205.

UTILITY

Figure 1:
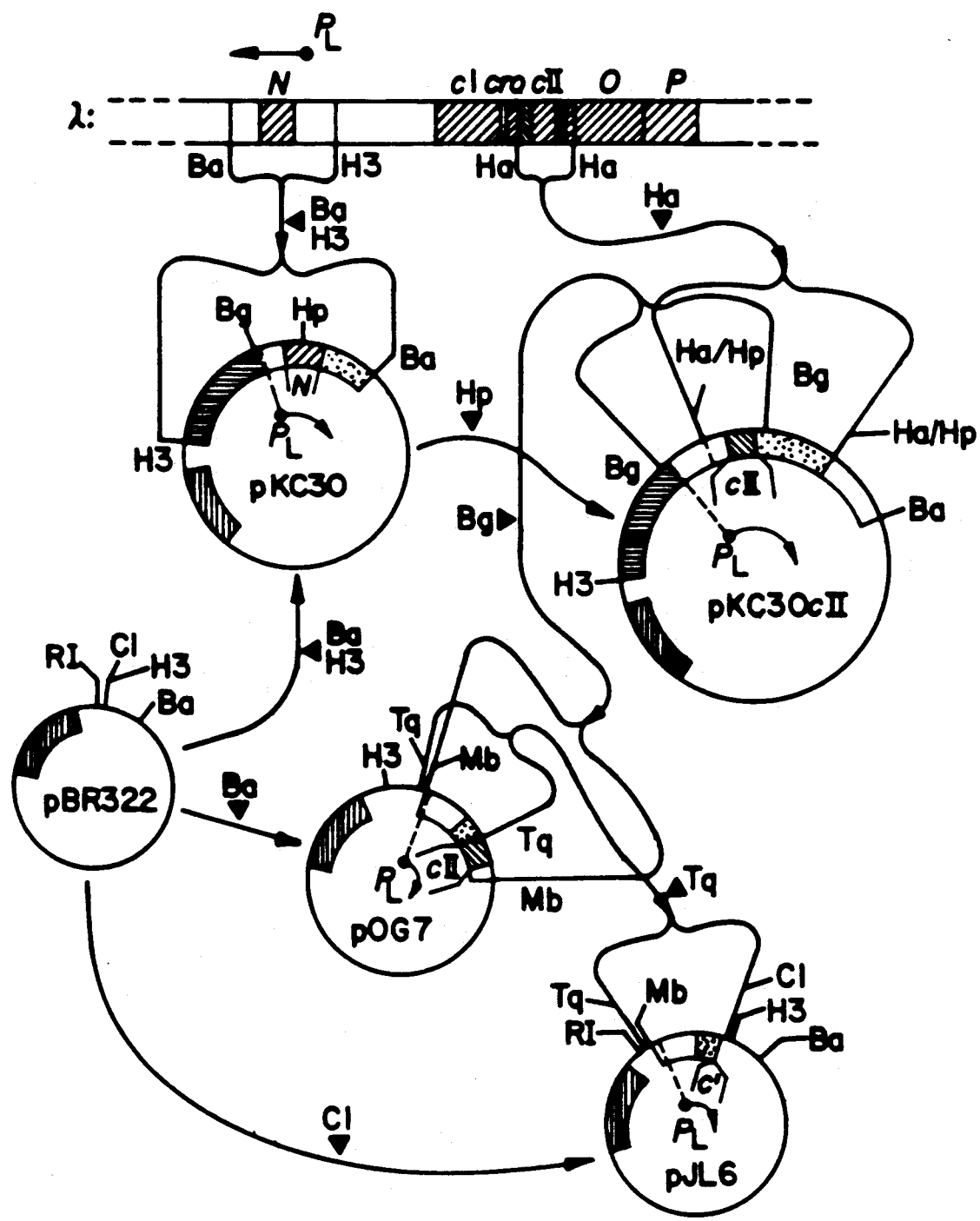
FIG. 1 shows the derivation of pJL6. 736-bp Taq I fragment of plasmid pOG7 containing phage λ $P_L$ promoter and amino-terminal end of phage λ cII gene was placed into Cla I site of plasmid pBR322. Recombinant plasmid, pJL6, contains an insert so oriented that the direction of transcription from $P_L$ promoter is opposite the direction of transcription of pBR322 β-lactamase message. Solid segments are ampicillin-resistance genes. Hatched segments indicate coding regions of phage λ. Heavily dotted segments indicate the region of phage λ DNA containing $P_L$ promoter. Finely dotted segments denote the region of phage λ DNA containing cII gene. c', amino-terminal fragment of phage λ cII gene; Ba, BamHI; Bg, Bgl II; Cl, Cla I; Ha, HaeIII; Hp, Hpa I; H3, HindIII; Mo, Moo I; RI, EcoRI; Tq, Taq I.

The vector of this invention facilitates the production of antibodies reactive to a wide assortment of oncogenes by significantly enhancing the expression of proteins in bacteria. This vector, like pBR322, is a superior cloning vehicle for the in vitro insertion of a gene specifying a desired phenotype into bacteria.

Advances in recombinant DNA technology have allowed investigators to search for unknown proteins starting from a known gene structure. Much of this work has involved raising antibodies to chemically synthesized peptides whose sequences are subsets of protein sequences predicted from the DNA sequence of the gene being studied. The development of efficient bacterial protein expression systems such as the one described here makes the technique of introducing eukaryotic or viral genes into bacteria an attractive alternative to the use of synthetic peptides since a single chimeric protein synthesized in bacteria may express determinants equivalent to twenty or more peptides. Since chimeric proteins synthesized in the most efficient bacterial expression systems can be directly found by inspection of stained gels, the isolation of bacterial colonies expressing a foreign protein does not require an immunological or enymatic assay for that protein.

The processes and uses of plasmid vehicles and the insertion of exogenous genes into bacterial cells is well known in the art. See Cohen et al (U.S. Pat. No. 4,237,224). A generalized description of the process is as follows: The essence of the process is transforming bacteria with a plasmid chimera. The bacteria must be one capable of being transformed by the plasmid. The plasmid chimera consists of a vector containing DNA sequences capable of being transformed in the bacteria (i.e., the replicon, or sequences of replication) and at least one foreign gene joined or annealed to the replicon. The vector and the foreign gene are covalently bonded in vitro to form a circularized plasmid structure, or alternatively, linearized DNA sequences. The bacteria is transformed under transforming conditions with the plasmid chimera. The chimera will then be replicated by the bacteria cells and cloned in vivo by growing the bacteria in a suitable growth medium. Cloning of the transformed bacteria allows the expression of the genotypical trait of the foreign gene.

The present invention is a process and composition consisting of transforming bacteria with cII-exogene gene fusion product that makes higher levels of the expected chimeric protein than processes previously known. This protein elicits exogene-specific antibodies in inoculated animals.

THE EXPRESSION VECTOR pJL6

The plasmid pOG7 of Oppenheim et al., *J. Mol. Biol.*, 158 (1982) 327-346, has many properties that are desirable in a vector suitable for high-level expression of exogenous proteins. It contains an efficient promoter and an efficient protein synthesis initiation site. Because large amounts of a foreign protein may be toxic to the bacterial host, it is desirable that the promoter be repressible. When the λ cII gene is placed in a plasmid under the control of the $P_L$ promoter (as it is in pOG7), very little cII protein is made when the promoter is repressed. In the absence of functional repressor, however, the cII protein is synthesized at a level of 5% of total cell protein. A useful expression vector should have a unique restriction site at a point where foreign genes can be inserted so as to be expressed at a high level. This is not true of pOG7—all known restriction enzymes that cleave within the cII gene on this plasmid also cleave the plasmid elsewhere.

To express oncogene sequences in *E. coli*, plasmid pOG7 was modified by inserting a 736-bp Taq I fragment from this plasmid into the Cla I site of pBR322. This Taq I fragment contains the entire phage λ $P_L$ promoter and the amino-terminal portion of the phage cII gene.

In general, MC29 is an acute leukemia virus responsible for a broad spectrum of malignant diseases including myelocytomas, renal and liver tumors, carcinomas, and sarcomas. The virus lacks functional gag, pol, and env genes, thus requiring a non-defective helper virus in order to replicate. The oncogenic properties of this virus are determined by a region of DNA sequences designated v-myc, sequences closely related to those of a genetic locus designated c-myc found in all vertebrate cells.

To construct the plasmid of this invention, plasmid pOG7 is modified by inserting two segments of bacteriophage λ DNA from pOG7 into plasmid pBR322 adjacent to each other. One of these segments contains the phage λ $P_L$ promoter while the other contains the structural gene for the phage protein λ cII (see FIG. 1). Since the $P_L$ promoter and the cII translation initiation site are both very efficient, cells containing this plasmid are capable of making large amounts of the cII protein. This plasmid pJL6, possesses a unique Cla I restriction site within the amino-terminal portion of the cII gene. This site represents a point for insertion of foreign genes—subjecting the foreign genes to the same transcriptional and translational controls as the cII gene on the plasmid pOG7. A restriction fragment containing the carboxy-terminal sequences compatible with the amino-terminal portion of the cII gene can be inserted in order to form a fusion hybrid gene. Bacteria containing a plasmid with such gene fusion makes higher levels of the expected chimeric protein than is produced by the conventional methods.

The experiments described in Examples 1-3 made use of cohesive end ligation of DNA fragment with pJL6 DNA to express a gene product at a high level. This was possible because the cII gene fragment on pJL6 and the MC29 v-myc gene both were found to possess ClaI sites that are cleaved in the same frame in relation to the codons that specify the respective proteins. The plasmid pJL6 is also used to express genes that lack such a ClaI site. For example, a restriction fragment containing a target gene can be enzymatically resected by exonuclease III and S2 nuclease so as to produce a population of molecules containing blunt ends terminated in all three frames near the beginning of the gene. These molecules may be ligated to ClaI linkers and then treated with ClaI to produce ClaI cohesive ends. This DNA can then be placed into ClaI-cleaved pJL6 cohesive end ligation. Many of the resultant plasmids contain a fusion between the cII gene fragment on pJL6 and the novel gene. One third of such plasmids express the novel gene since that proportion of them should have the fusion in the correct frame.

SPECIFIC DISCLOSURE

Bacterial strains. *E. coli* N4830 and N4831 have been described by Gottesman et al., *J. Mol. Biol.*, 140 (1980), 57-75. N4830 harbors a heavily deleted phage λ prophage carrying the mutant c1857 temperature sensitive repressor and an active N gene. N4831 is isogenic with N4830 except that the prophage N gene in N4831 is inactive due to the presence of two amber mutations (Nam7, Nam53). DC646 is a derivative of *E. coli* C600$r_K$-$m_K$+ made lysogenic for phage λ. This strain possesses *E. coli* K-12 DNA modification activity but does not restrict DNA.

Figure 2:
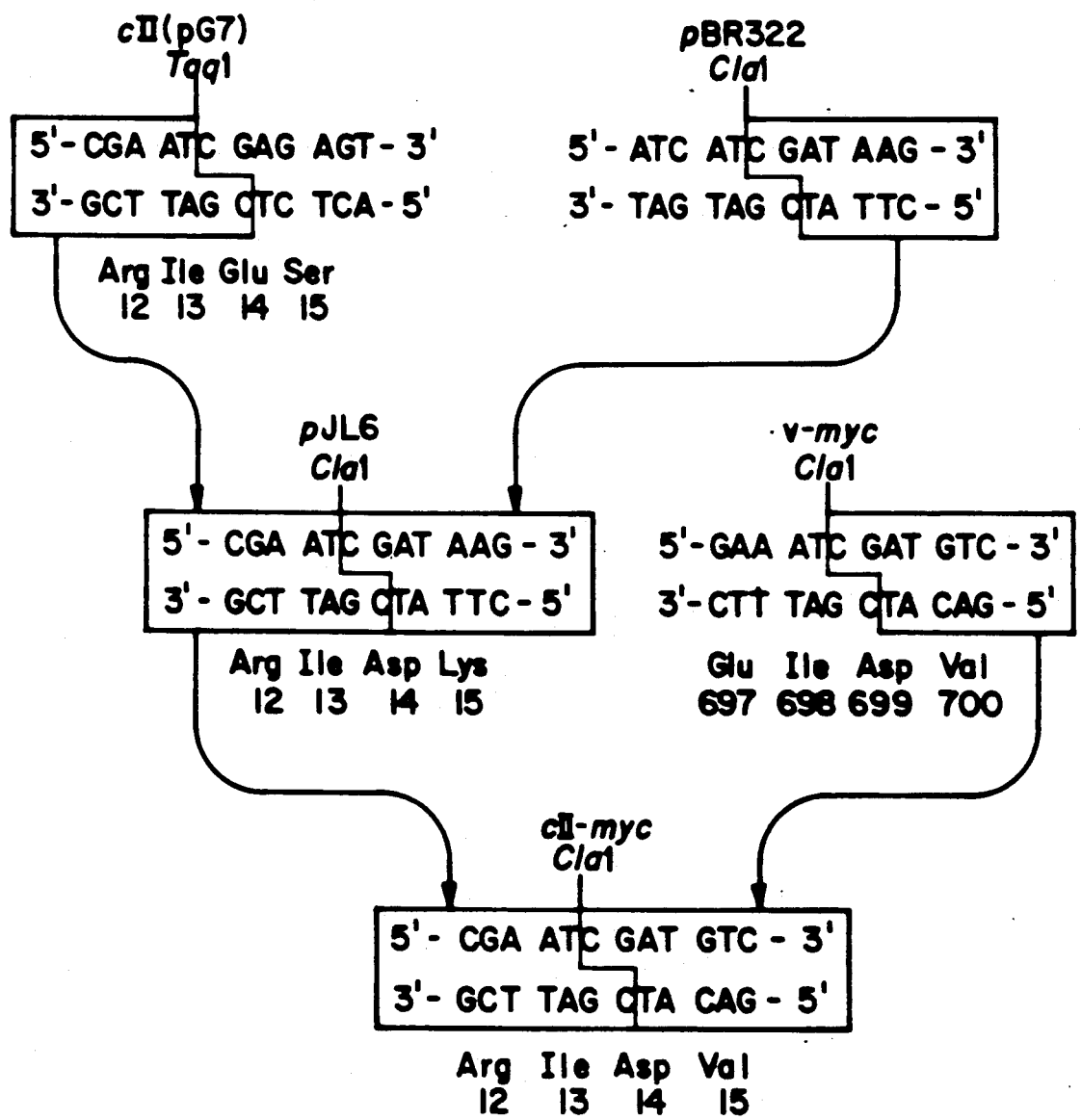
FIG. 2 shows the sequences of regions involved in construction of pJL6 and pJLcIImyc1. Translation read-through from cII gene into pBR322 sequence in pJL6 would result in peptide containing 16 amino acid residues. Amino acids shown are numbered from cII gene initiation codon (cII and pJL6 and cII-myc) or initiation codon of MC29 P110$^{gag\text{-}myc}$ (v-myc).

Plasmid. Plasmid pOG7 was produced by Oppenheim et al., *J. Mol. Biol.*, 158 (1982), 327-346, by subcloning a BglII fragment of pKC30cII that contained the $P_L$ promoter and cII gene into the BamHI site of plasmid pBR322. The 736-bp Taq I fragment of plasmid pOG7 containing the phage λ $P_L$ and the amino-terminal end of the phage λ cII gene was placed into the ClaI site of plasmid pBR322. As shown in FIG. 2, fusion of the end of this fragment (next to the cII gene) with a ClaI-generated end of pBR322 DNA results in a junction that can be cleaved by ClaI. The insert thus placed in recombinant plasmid pJL6 is oriented so that the direction of the transcription from the $P_L$ promoter was opposite from the direction of transcription of the pBR322 β-lactamase message.

Preparation of DNA. Plasmid DNAs were prepared as described by Birnboim and Doly, *Nucl. Acids Res.*, 7, pp 1513-1523 (1979), from 5-ml cultures for screening or from 1-liter cultures for preparation of restriction fragments. Plasmid DNA from the larger cultures was further purified by ethidium bromide-CsCl banding.

Construction of recombinant plasmids. Plasmid DNAs were cleaved by the appropriate restriction enzymes and subjected to electrophoresis on polyacrylamide gels. Fragments were eluted from the gels by the method of Maxam and Gilbert, *Methods of Enzymology*, Vol. 65, Academic Press, New York, pp 499-560 (1980). Vector DNA was prepared for ligation by cleavage with the appropriate restriction enzymes and treated with calf intestinal phosphatase (Boehringer).

Ligation of each isolated fragment (0.5 μg) to vector DNA (1.6 μg) was performed in 66 mM Tris.HCl, pH 7.4 mM MgCl$_2$, 10 mM dithiothreitol, 0.4 mM ATP, and 2.5 units/ml T4 DNA ligase. The reactions (0.04 ml) were incubated at 4° C. for 18 h. Calcium chloride-treated E. coli DC646 cells were transformed as described (Cohen et al., Proc. Natl. Acad. Sci. USA, Vol. 69, pp 2110–2114, 1972) and ampicillin-resistant colonies were screened for plasmids.

Radiolabelling and electrophoresis of bacterial proteins. E. coli cells were grown at 32° C. in M56 minimal media supplemented with 0.5% glucose, 0.01% each of all amino acids except methionine and cystine, 0.01% biotin, 0.01% thiamine and 50 umg/ml ampicillin. When the A$_{590}$ of the cultures reached 0.2, the temperature was shifted to 41° C. Aliquots (150 μl) of the cells were taken 5 min. before and at 10 min. and 30 min. after the temperature shift. These cells were added to 15 ul of media containing 2.5 μCi [$^{35}$S]-cystine (NEN, 330 mCi/mmol) and incubated for 1.5 min. After labeling, some cultures were chased by adding unlabeled cystine to a final concentration of 0.5 mM. Cellular protein was precipitated with 10% (w/v) trichloroacetic acid, washed with acetone, and resuspended in 1.0% SDS/0.1% β-mercaptoethanol. The proteins were then resolved by electrophoresis on 10% SDS-polyacrylamide gels and visualized by autoradiography.

Preparation of bacterial extracts. Unfractionated extracts were prepared from cells grown at 32° C. in supplemented M56 media to an A$_{590}$-0.3. The cultures were then induced by shaking another 60 min. at 41° C. The cells were pelleted by centrifugation, resuspended in 1/40 vol. supplemented M56 media and heated for 20 min. at 95° C. after being brought to a final concentration of 0.7% SDS and 0.07% β-mercaptoethanol. Briefly, the induced bacteria were pelleted by centrifugation and resuspended in 50 mM Tris.HCl, pH 8.0, in 25% sucrose. Lysozyme was added to a final concentration of 2 mg/ml. After 5 min. at 0° C., MgCl$_2$ was added to 5 mM final concentration, followed by DNase I to 60 μg/ml. The cells were lysed by the addition of 1% NP40/0.5% sodium deoxycholate/0.1M NaCl/0.01 mM Tris.HCl, pH 7.2/1 mM EDTA and centrifuged at 12000×g for 10 min. The pelleted material was washed with 1M NaCl/10 mM Tris.HCl, pH 7.2/1 mM EDTA and resedimented. The resultant pellet was resuspended in 1% SDS/0.1% β-mercaptoethanol by being heated for 10 min. at 95° C. This resuspended material is designated the "high-salt-pellet fraction."

As has been described above, the plasmid pJL6 contains a ClaI site beyond the bacteriophage λ cII gene initiation codon. This site permits the fusion of the carboxy-terminal sequences of an exogene to the amino-terminal portion of the cII gene. Transcription of the hybrid gene, the fusion product, is controlled from the phage λ P$_L$ promoter. When this promoter is derepressed, E. coli cells transformed with the chimeric plasmid produce high levels of the cII-exogene fusion protein. The examples show experiments in which the exogene is myc, myb, or ras gene sequences. However, this invention is not limited thereby; any exogene containing carboxy-terminal sequences may be inserted in plasmid pOG7's ClaI site.

EXAMPLE 1

A MC29 v-myc was inserted as the exogenous gene. A ClaI site occurs within the myc region of MC29 that is cleaved between the second and third base of a codon used to specify P110$^{gag-myc}$. The ClaI site in pJL6 at the end of the phage λ cII gene fragment also was cleaved between the second and third base of a codon. Ligation of ends terminated at these ClaI sites thus results in a fusion of these genes such that protein synthesis initiated in the cII gene continues into the v-myc gene in the correct reading frame (FIG. 2). Plasmid pJL6 contains a short nonessential DNA segment between its unique ClaI and BamHI sites that can be readily replaced by other ClaI-BamHI fragments. It was thus possible to insert a 980-bp Cla-BamHI fragment containing the 3' end of the v myc gene into pJL6 so as to create a cII-myc gene fusion of the type discussed above. Two independent but apparently identical plasmids found to have the expected cII-myc gene fusion were designed pJLcIImyc1 and pJLcIImyc2. The predicted DNA and amino acid sequences at the cII-myc junction are shown in FIG. 2.

Plasmids containing the cII-myc gene fusion were transformed into N4830. This bacteria strain contains a λ prophage that has a temperature sensitive mutation (c1857) in the c1 repressor gene. At 32° C. the repressor is active and the P$_L$ promoter on the plasmid is repressed. At 41° C. the repressor is inactive and the P$_L$ promoter is induced. Lysogens carrying the cII-myc plasmid were grown at 32° C. and bacterial proteins were labeled with [$^{35}$S]-cystine before and after induction at 41° C. The cells were lysed and the total mixture of cellular protein was resolved on an SDS-polyacrylamide gel. Cells induced for 10 min. and 30 min. synthesize an M, 23 500 protein not made by uninduced cells. This is close to the size expected for the predicted cII-myc fusion protein. The protein is somewhat unstable in cells since the quantity of labeled protein was diminished after a chase with excess unlabeled cystine.

EXAMPLE 2

The cII-myc fusion plasmids of Example 1 were also transformed into N4831. The prophage carried by N4831, unlike the one harbored by N4830, has an inactive N gene. The level of synthesis of the cII-myc fusion protein from the plasmids was much less in N4831 cells than in N4830 cells (data not shown). Shimatake and Rosenberg, Nature, 292, pp 128–132 (1981), have observed that when the cII gene is under the control of the P$_L$ promoter on pKC30cII, the N gene product is required for a high level of expression. This is because the gene N protein is required to antiterminate transcription at the transcription termination site, t$_{R1}$, located just upstream from the start of the cII gene. Since the gene for the cII-myc fusion protein on pJLcI-Imyc1 is under the control of the same regulatory sequences as the cII gene on pKC30cII, the finding that high level synthesis of the M, 23 500 protein requires the gene N protein provides further evidence that this protein is the expected cII-myc fusion protein.

EXAMPLE 3

To determine if the cII-myc protein shared antigenic properties with the MC29 P110$^{gag-myc}$, polyacrylamide gel slices containing the cII-myc fusion protein were homogenized and injected into rabbits. An M, 110 000 protein found in the MC29-infected Q8 cells is immunoprecipitated by the sera collected from these animals. This protein precisely comigrates with P110a$^{gag-myc}$. Therefore, the cII-myc protein synthesized in E. coli shares antigenic determinants with an authentic v-myc gene product. P110$^{gag-myc}$ was not observed when extracts of uninfected Japanese quail cells were immunoprecipitated with the rabbit anti-cII-myc sera or when the Q8 cell extracts were immunoprecipitated with sera taken from the rabbit prior to immunization with the cII-myc fusion protein.

EXAMPLE 4

Figure 3:
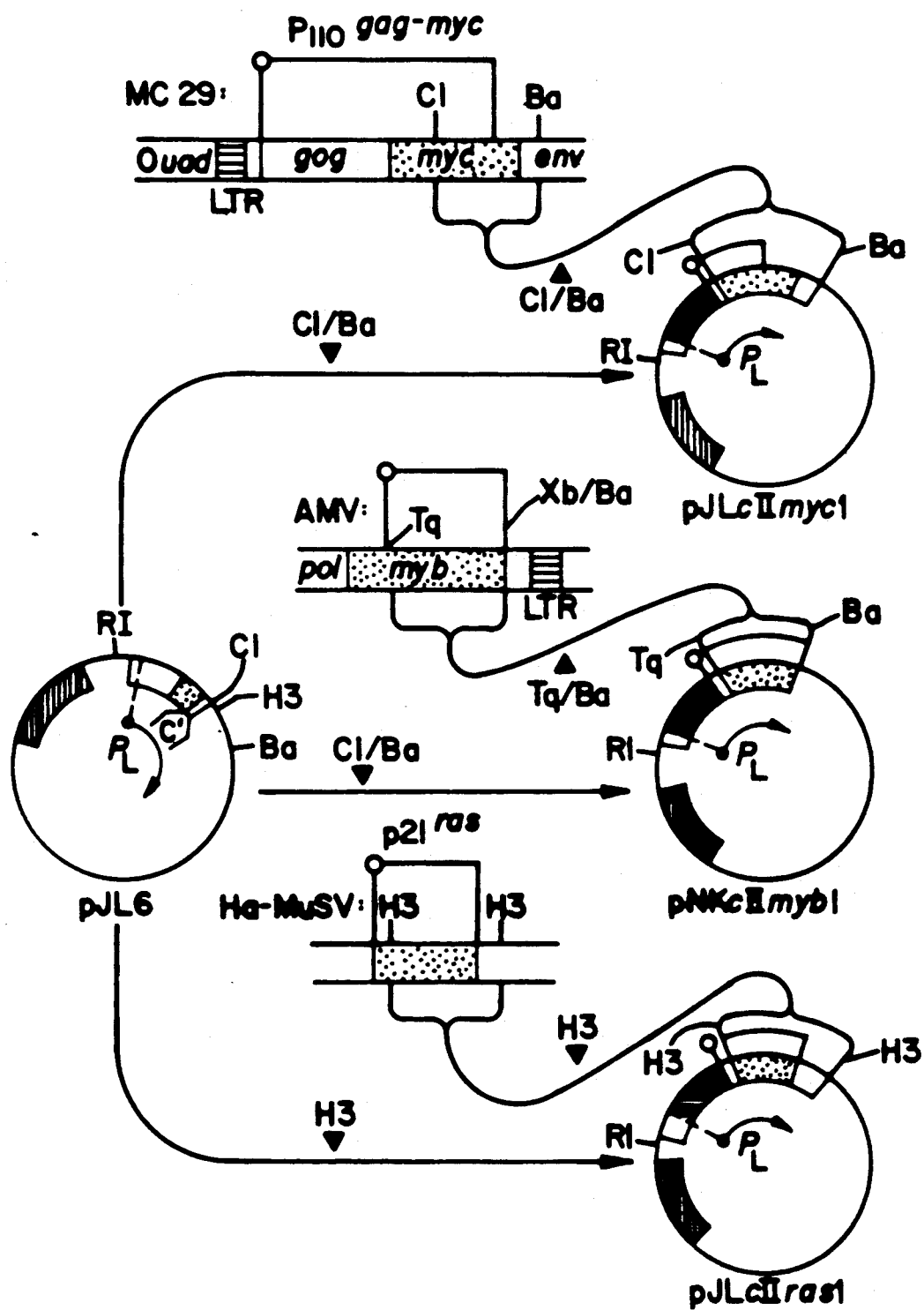
FIG. 3 shows the construction of expression plasmids containing myc, myb, or ras sequences. 980-bp Cla I-BamHI fragment containing carboxy-terminal portion of v-myc gene was isolated from pBR322 subclone of MC29-1 that contained 2.9-kb BamHI fragment extending from gag to env portion of cloned MC29 proviral sequences. This ClaI-BamHI fragment was inserted between ClaI and BamHI sites on plasmid pJL6 DNA to generate plasmid pJLcIImyc1. 785-bp Taq I-BamHI fragment containing v-myb sequences was isolated from plasmid pBR322/KX162. This fragment was inserted between ClaI and BamHI sites on plasmid pJL6 to generate pNKcIImyb1. 880-bp HindIII fragment containing most of Ha-MuSV ras gene was isolated from plasmid H1 and inserted into HindIII site of pJL6 to generate pJLcIIras1. Solid segments, ampicillin-resistance genes. Heavily dotted segments, DNA derived from phage λ. Finely dotted segments, oncogene DNA. Cross-hatched segments, LTR regions of proviral DNA. Ba, BamHI; Cl, ClaI; H3, HindIII; RI, EcoRI; Tq, Taq I; Xb, Xba I.

The sequence of the AMV v-myb gene contains a single long ORF. This in itself may code for the AMV transforming protein or may code for the carboxyterminal sequences of a protein translated from a spliced message. A 785-bp Taq I-BamHI fragment containing most of this long ORF was isolated from plasmid pBR322/KX162 and ligated into pJL6 cleaved by ClaI-BamHI. The Taq I end of the fragment was near the first ATG in the long ORF. Taq I cleaves this site between the second and third bases of a codon of this ORF, and Cla I also cleaves the phage λ cII gene in pJL6 between the second and third bases of a codon. Because Taq I and Cla I produce ends suitable for cohesive end ligation, the fusion of the Cla I end of pJL6 and the Taq I end of the 785-bp Taq I-BamHI fragment from myb results in a gene fusion that allows expression initiating in the phage λ cII gene in pJL6 to continue into the AMV v-myb ORF. A plasmid containing this fusion was designated pNKcIImyb1 (see FIG. 3).

EXAMPLE 5

The principal product of the Ha-MuSV ras gene is an $M_r$ 21,000 protein ($p21^{ras}$). The sequence of v-ras$^{Ha}$ predicts that HindIII cleaves between the first and second bases of the fifth codon of the sequences that specify $p21^{ras}$. Because the Cla I site on pJL6 is adjacent to a HindIII site, translation initiating at the beginning of the phage cII gene should read past the Cla I site and through the HindIII site. HindIII cuts between the first and second bases of a codon in frame with the cII initiation codon, so it was possible to create an in-frame gene fusion between cII and ras by ligating a HindIII fragment containing most of the ras gene to HindIII-cleaved pJL6. The 890-bp HindIII fragment containing the ras$^{Ha}$ gene was from plasmid H1 of Chang et al., *J. Virology*, Vol. 35, pp 76-92 (1980). Two plasmids having cII and ras in the same orientation were designated pJLcIIras1 (see FIG. 3) and pJLcIIras2. Two plasmids having cII and ras in the opposite orientation were pJLcIIsar1 and pJLcIIsar2.

*Escherichia coli* transformants containing pJL6 have been deposited as ATCC Deposit No. 53456 at The American Type Culture Collection, 12301 Parklawn Drive, Rockville, Md. 20852 on 31 Jan. 1986.

We claim:

1. Recombinant plasmid pJL6 characterized as shown in FIGS. 1 and 2.

2. The recombinant plasmid of claim 1, comprising a $P_L$ promoter region adjacent to a CII translation initiation site, wherein a ClaI restriction site is present in said CII initiation site.

3. A process for preparing the recombinant plasmid pJL6 of claim 12, which comprises placing the TaqI fragment of plasmid pOG7 containing the phage λ $P_L$ promoter and the amino terminal end of the phage λ cII gene into the ClaI site of plasmid pBR322.

4. In a process for producing a replicable cloning vehicle capable of expressing in a bacterial host a particular protein coded by an oncogene carried on the cloning vehicle, the improvement which comprises the steps of:
    a) inserting a TaqI fragment of plasmid pOG7 containing the phage λ $P_L$ promoter and the amino terminal end of the phage λ CII gene into the ClaI site of plasmid pBR322;
    b) cleaving with ClaI restriction enzyme the ClaI side of an oncogene to expose a carboxy terminal end; and
    c) joining the amino terminal end of step (a) with the carboxy terminal end of step (b) to form a recombinant plasmid containing an oncogene.

5. The process of claim 4 in which the oncogene contains 480 base pair myc sequence.

6. The process in claim 4 in which the oncogene contains 785 base pair myb sequence.

7. The process in claim 4 in which the oncogene contains 890 base pair ras sequence.

8. A method for producing high levels of protein using a transformed bacterial host which comprises:
    fusing the carboxy terminal end of an oncogene to the amino terminal end of the phase λ cII gene on plasmid of claim 2;
    transforming a suitable bacterial host with said plasmid; and
    culturing the transformed bacterial host to secrete the protein coded by the oncogene.

9. The method of claim 8 in which the oncogene is myc gene.

10. The method of claim 8 in which the oncogene is myb gene.

11. The method of claim 8 in which the oncogene is ras gene.

* * * * *